June 28, 1960 R. W. CUMMING Plant Pat. 1,956
CHRYSANTHEMUM PLANT
Filed Oct. 1, 1959
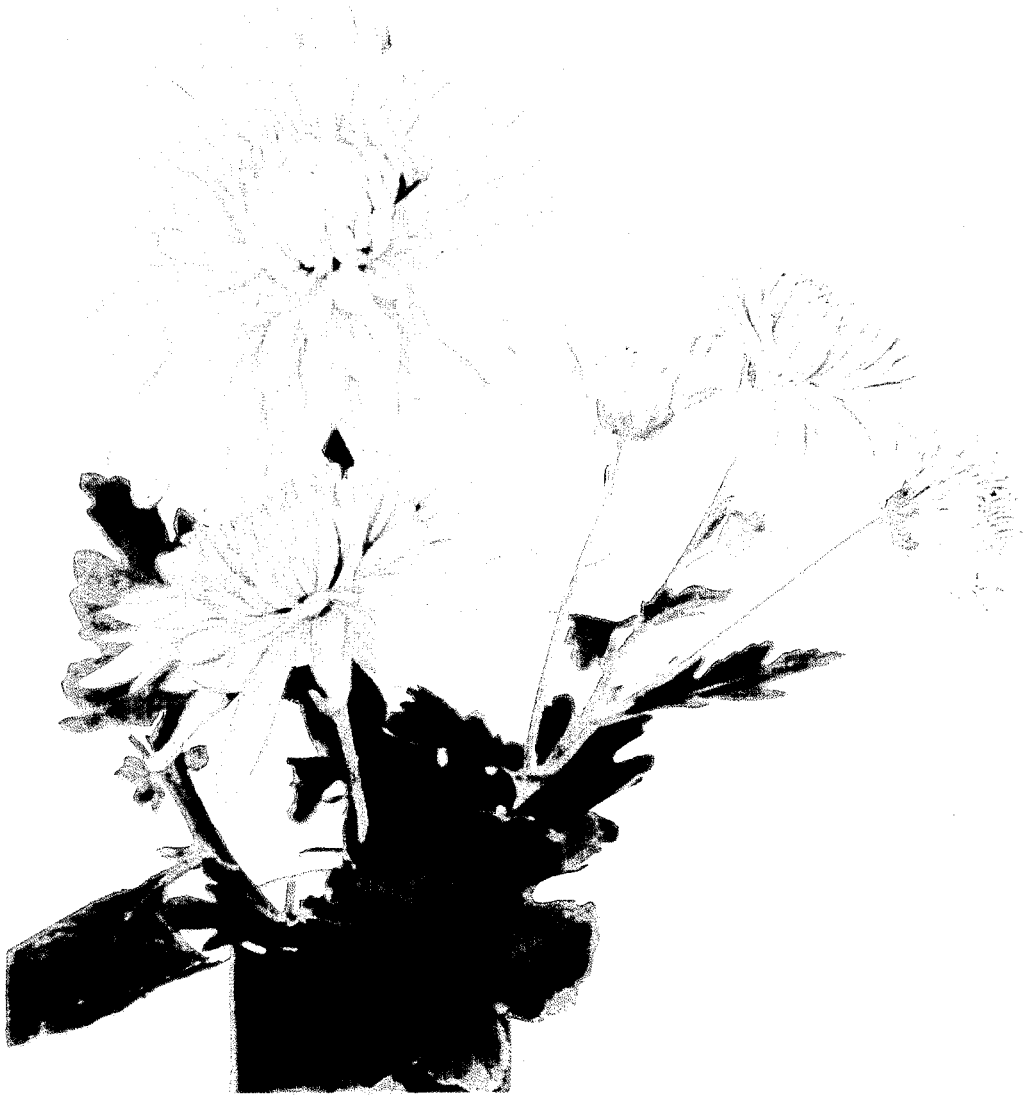
Inventor.
R. W. Cumming
By: Robb & Robb
Attorneys.

United States Patent Office

Plant Pat. 1,956
Patented June 28, 1960

1,956

CHRYSANTHEMUM PLANT

Roderick W. Cumming, Bristol, Conn., assignor to Bristol Nurseries, Inc., Bristol, Conn., a corporation of Connecticut Filed Oct. 1, 1959, Ser. No. 843,901

1 Claim. (Cl. 47—60)

The present invention relates to a new and distinct variety of chrysanthemum plant of the decorative class, which was originated by me by crossing the variety "Coppersmith" (unpatented) with the variety "Crowning Glory" (unpatented).

The primary objective of this breeding was to produce a new variety of chrysanthemum in which there is combined the general features of an upright growth habit, an early blooming habit, individual flowers of large size, and a novel general color tonality falling into an intermediate color range. This objective was fully achieved, along with other desirable improvements, as evidenced by the following unique combination of characteristics which are outstanding in the new variety and which distinguish it from its parents as well as from all other vareties of which I am aware:

(1) An upright habit of plant growth;

(2) Good winter hardiness, and good frost resistance of the flowers;

(3) Very healthy, glossy, Dark Green foliage which remains on the plant all the way to the ground;

(4) Strong flower stems;

(5) Heavy flower production;

(6) An early blooming habit, with attending long period of flower display;

(7) Flowers of unsually large size and decorative form, with the flower petals tending to slightly recurve;

(8) A habit of bearing the flowers in superb sprays suitable for cutting; and (9) A distinctive Salmon Buff, blended with Capucine Buff and Light Coral Red, general color tonality of the flowers.

Asexual reproduction of the new variety by top cuttings, as performed by me at Bristol, Connecticut, shows that these characteristics and distinctions come true to form and are established and transmitted through succeeding propagations.

The accompanying drawings shows typical specimens of the vegetative growth and flowers of my new Chrysanthemum variety in various stages of development, and as depicted in color as nearly true as it is reasonably possible to make the same in a color illustration of this character.

The following is a detailed description of the new variety, with color terminology in accordance with Ridgway's Color Standards and Nomenclature, as based upon observations made from specimens grown outdoors at Bristol, Connecticut, in the late morning in late September.

Parentage: "Coppersmith" × "Crowning Glory."

Classification: Decorative.

Growth: Upright; full; attains a height of approximately 24 inches.

Cold resistance: Winter hardy in central Connecticut under normal winter protection; flowers are quite resistant to frost.

Blooming period: In the Bristol, Connecticut climatic area, flower display usually starts about September 25, and continues until extreme freezing weather.

*Flower*

Bud:

*Color.*—When sepals first divide: outside—Warm Buff, Plate XV, blended Light Ochraceous-Salmon, Plate XV; inside—Coral Red, Plate XIII, blended with Jasper Red, Plate XIII. When petals begin to unfurl: Light Ochraceous-Buff, Plate XV, blended with Warm Buff, Pate XV. When half-blown: Inside of outer petals—Undertone of Warm Buff, Plate XV, blending into tones of Coral Red, Plate XIII and Jasper Red, Plate XIII; Reverse of petals Light Ochraceous-Buff, Plate XV, blending throughout with Coral Red, Plate XIII.

*Peduncle.*—Strength—strong. Color—Leaf Green, Plate XII, tinged with Vinaceous Lilac, Plate XLIV.

Bloom:

*Size.*—Average about 3½ inches, but occasionally larger.

*Stem.*—Strong; erect.

*Form.*—Decorative.

*Petalage.*—Double.

*Color.*—Center of flower—Light Ochraceous-Salmon, Plate XV, highlightted with Antimony Yellow, Plate XV. Intermediate petals—upper face: Salmon Buff, Plate XIV, blended with Light Coral Red, Plate XIII, with depth color Jasper Red, Plate XIII; reverse face: Light Ochraceous-Buff, Plate XV, blended with Mustard Yellow, Plate XVI. Outer petals—Capucine Buff, Plate III, blended throughout to Light Coral Red, Plate XIII.

*Petals.*—Texture—firm, when placed in water. Form—Long (up to 3 inches in full length); strap-like; often recurving.

*Fragrance.*—Pronouncedly typical of chrysanthemums.

*Plant*

Form: Medium height; somewhat like an inverted pyramid or cone.

Growth: Strong; compact; free.

Foliage:

*Size.*—Large (from 3 to 4 inches long).

*Quantity.*—Well above normal.

*Form.*—Shallowly cut.

*Color.*—Upper side—Danube Green, Plate XXXII. Reverse side—Deep Dull Yellow-Green (2), Plate XXXII.

I claim:

A new and distinct variety of chrysanthemum plant of the decorative class, substantially as herein shown and described, characterized particularly as to novelty by the unique combination of an upright habit of plant growth, good winter hardiness and good frost resistance of the flowers, very healthy, glossy, Dark Green foliage which remains on the plant all the way to the ground, strong flower stems, heavy floral production, an early blooming habit with attending long period of flower display, flowers of unusually large size and decorative form, with the flower petals tending to slightly recurve, a habit of bearing the flowers in superb sprays that are suitable for cutting, and a distinctive Salmon Buff, blended with Capucine Buff and Light Coral Red, general color tonality of the flowers.

No references cited.